(12) United States Patent
Hulme

(10) Patent No.: US 11,642,447 B2
(45) Date of Patent: May 9, 2023

(54) REVERSE OSMOSIS WATER SYSTEM WITH HEAT FORWARD FUNCTION

(71) Applicant: Evoqua Water Technologies LLC, Pittsburgh, PA (US)

(72) Inventor: Clinton W. Hulme, Pennsburg, PA (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 296 days.

(21) Appl. No.: 16/755,760

(22) PCT Filed: Oct. 16, 2018

(86) PCT No.: PCT/US2018/056049
§ 371 (c)(1),
(2) Date: Apr. 13, 2020

(87) PCT Pub. No.: WO2019/079274
PCT Pub. Date: Apr. 25, 2019

(65) Prior Publication Data
US 2020/0276374 A1  Sep. 3, 2020

Related U.S. Application Data

(60) Provisional application No. 62/573,447, filed on Oct. 17, 2017.

(51) Int. Cl.
*A61L 2/04* (2006.01)
*A61L 2/24* (2006.01)
(Continued)

(52) U.S. Cl.
CPC ............. *A61M 1/1686* (2013.01); *A61L 2/04* (2013.01); *A61L 2/24* (2013.01); *A61M 1/1656* (2013.01);
(Continued)

(58) Field of Classification Search
CPC .............. A61M 1/1686; A61M 1/1656; A61M 2205/3334; A61M 1/155; A61M 1/1601;
(Continued)

(56) References Cited

U.S. PATENT DOCUMENTS 4,166,031 A   8/1979  Hardy
5,591,344 A   1/1997  Kenley et al.
(Continued)

FOREIGN PATENT DOCUMENTS

CN   205999072 U   3/2017
FR      2465983      3/1981
(Continued)

OTHER PUBLICATIONS

International Search Report and Written Opinion of the International Searching Authority dated Dec. 13, 2018 of International PCT Application No. PCT/US2018/56049 filed Oct. 16, 2018.
(Continued)

*Primary Examiner* — Joseph W Drodge

(57) ABSTRACT

A reverse osmosis (RO) system is described that is connectable to a dialysis machine and is capable of using heated purified water to clean and disinfect an external connection section or portion disposed between the RO system and the dialysis unit (or any other external heat tolerant device) without forming a closed loop system between both systems before and during a heat forward process. This can be accomplished without the need for direct/indirect or wired/wireless communication with the dialysis unit or the need to introduce a chemical cleaner or process that would require further rinsing after chemical disinfection.

5 Claims, 6 Drawing Sheets

(51) Int. Cl.
  *A61M 1/16* (2006.01)
  *B01D 61/02* (2006.01)
  *B01D 61/12* (2006.01)
  *C02F 1/02* (2023.01)
  *C02F 1/44* (2023.01)

(52) U.S. Cl.
  CPC .......... *B01D 61/025* (2013.01); *B01D 61/12* (2013.01); *C02F 1/02* (2013.01); *C02F 1/441* (2013.01); *A61L 2202/11* (2013.01); *B01D 2311/06* (2013.01); *B01D 2311/103* (2013.01); *C02F 2209/02* (2013.01); *C02F 2209/03* (2013.01); *C02F 2209/40* (2013.01); *C02F 2303/16* (2013.01)

(58) Field of Classification Search
  CPC ........ A61M 1/1605; A61M 2205/3331; A61M 2205/3341; A61M 2205/3351; A61M 2205/3368; A61M 2205/3379; A61M 2206/10; A61L 2/04; A61L 2/24; A61L 2202/11; A61L 2202/14; A61L 2202/24; A61L 2/26; B01D 61/025; B01D 61/12; B01D 2311/06; B01D 2311/103; B01D 61/06; B01D 61/10; B01D 2221/10; B01D 2221/14; B01D 2311/10; B01D 2311/16; B01D 2313/08; B01D 2313/18; B01D 2313/22; B01D 2313/243; B01D 2313/38; B01D 65/02; B01D 65/022; B01D 65/027; C02F 1/02; C02F 1/441; C02F 2209/02; C02F 2209/03; C02F 2209/40; C02F 2303/16; C02F 2209/005; C02F 1/008; C02F 1/44; C02F 2301/02; C02F 2301/06; C02F 2303/04; F04B 49/00; F04B 49/10; F04B 49/103; F04B 49/20; F04B 49/22; F04B 2203/0204; F04B 2203/0404; F04B 2205/04; F04B 2205/09; F04B 2205/11; F04B 2207/03; F04B 2207/04; F04B 2207/041; F04B 2207/0411; F04B 2207/042; F04B 2207/045; F04C 14/00; F04C 14/24; F04C 14/28; F04C 28/24; F04C 2270/20; F04C 2270/58; F04C 2270/585; F04D 27/00; F04D 27/041; F04D 27/0412; F04D 27/042; F04D 27/045
  See application file for complete search history.

(56) References Cited

U.S. PATENT DOCUMENTS

| | | | |
|---|---|---|---|
| 6,099,735 | A | 8/2000 | Kelada |
| 6,246,831 | B1 | 6/2001 | Seitz et al. |
| 6,861,033 | B2 | 3/2005 | Mullins et al. |
| 7,210,601 | B2 | 5/2007 | Hortin et al. |
| 8,064,233 | B2 | 11/2011 | Ishizu et al. |
| 8,506,885 | B2 | 8/2013 | Kotsos et al. |
| 8,692,167 | B2 | 4/2014 | Hedmann et al. |
| 9,151,516 | B2 | 10/2015 | Buescher et al. |
| 9,322,258 | B2 | 4/2016 | Henson et al. |
| 9,358,331 | B2 | 6/2016 | Fulkerson et al. |
| 9,768,783 | B1 | 9/2017 | Schmit |
| 9,975,090 | B2 | 5/2018 | Hoffman |
| 10,099,179 | B2 | 10/2018 | Volker |
| 10,159,939 | B2 | 12/2018 | Volker |
| 10,207,225 | B2 | 2/2019 | Lutz et al. |
| 10,246,351 | B2 | 4/2019 | Völker |
| 10,668,201 | B2 | 6/2020 | Wrazel et al. |
| 11,235,990 | B2 * | 2/2022 | Hulme ........... C02F 1/02 |
| 2002/0100716 | A1 | 8/2002 | Bosko |
| 2003/0034305 | A1 | 2/2003 | Luehmann et al. |
| 2007/0102357 | A1 | 5/2007 | Weatherill |
| 2009/0035856 | A1 * | 2/2009 | Galliher ............ C12M 29/10 435/294.1 |
| 2009/0134080 | A1 * | 5/2009 | Fabig ............... C02F 1/441 210/181 |
| 2009/0304524 | A1 * | 12/2009 | Wilder ............. F04C 28/06 417/44.11 |
| 2011/0300231 | A1 * | 12/2011 | Peterson ......... A61M 1/1658 422/38 |
| 2013/0068674 | A1 * | 3/2013 | Manabe .......... C02F 1/441 210/103 |
| 2014/0151297 | A1 | 6/2014 | Hulme et al. |
| 2015/0027937 | A1 | 1/2015 | Katou et al. |
| 2015/0273090 | A1 | 10/2015 | Felding et al. |
| 2016/0256582 | A1 * | 9/2016 | Hertz ............. A61M 1/1688 |
| 2017/0197020 | A1 * | 7/2017 | Buckberry ........ C02F 1/008 |
| 2018/0236156 | A1 * | 8/2018 | Glaser ............ A61M 1/1686 |
| 2019/0083934 | A1 | 3/2019 | Moon et al. |
| 2019/0299163 | A1 | 10/2019 | Kim et al. |
| 2020/0329532 | A1 * | 10/2020 | Hulme ............ B01D 61/10 |

FOREIGN PATENT DOCUMENTS

| | | | |
|---|---|---|---|
| WO | 99/55448 | 11/1999 | |
| WO | 03/40042 | 5/2003 | |
| WO | 2007/0045015 | 4/2007 | |
| WO | 2015/100502 | 7/2015 | |
| WO | 2016/0086737 | 6/2016 | |
| WO | WO 2017/042319 | * 3/2017 | ............ C02F 1/44 |
| WO | 2017/171406 | 10/2017 | |
| WO | 2017/218932 | 12/2017 | |
| WO | 2018/036753 | 3/2018 | |

OTHER PUBLICATIONS

International Search Report and Written Opinion of the International Searching Authority dated Jan. 4, 2019 of International PCT Application No. PCT/US2018/56059 filed Oct. 16, 2018.
"Mar Cor Purification Introduces the Millenium HX," Mar Cor Purification, 3027803 Rev. A, 2 pp., 2012.
"Miilenium HX: Portable Water Purification System w/ Automatic Hot Water Disinfection," Mar Cor Purification, 3027573 Rev. C, 2 pp., 2012.
"Purification Millenium HX Reverse Osmosis Unit Operation and Maintenance Manual," Mar Cor Purification, 3026177 Rev. B, 154 pp., Apr. 16, 2012.
Gambro, WRO 300 Operator's Manual, Sep. 2010, pp. 11, 22 and 24 (accessed on Oct. 14, 2016 at https://www.manualslib.com/manual/439580/Gambro-Wro-300-H.html).
International Search Report and Written Opinion of the International Searching Authority dated Feb. 12, 2019 of International PCT Application No. PCT/US2018/56063 filed Oct. 16, 2018.
International Preliminary Report on Patentability of the International Searching Authority dated Apr. 30, 2020 of International PCT Application No. PCT/US18/56049 filed Oct. 16, 2018.
International Preliminary Report on Patentability of the International Searching Authority dated Apr. 30, 2020 of International PCT Application No. PCT/US18/56059 filed Oct. 16, 2018.
International Preliminary Report on Patentability of the International Searching Authority dated Apr. 30, 2020 of International PCT Application No. PCT/US18/56063 filed Oct. 16, 2018.

* cited by examiner

REVERSE OSMOSIS WATER SYSTEM WITH HEAT FORWARD FUNCTION

CLAIM OF PRIORITY

This application claims priority to and the benefit of U.S. Provisional application with Ser. No. 62/573,447, filed on Oct. 17, 2017, entitled PORTABLE REVERSE OSMOSIS WATER PURIFICATION SYSTEM, which is herein incorporated by reference in its entirety.

CROSS-REFERENCE TO RELATED APPLICATIONS

This application relates to U.S. Patent Publication No. 2014/0151297, filed on Nov. 27, 2013, and entitled "Portable Reverse Osmosis Water Purification System," the disclosure of which is incorporated by reference.

TECHNICAL FIELD

The present disclosure relates to water purification systems. More specifically, the present disclosure relates to a portable reverse osmosis water purification system.

BACKGROUND

Reverse osmosis (RO) is a filtration method that removes many types of large molecules and ions from solutions by applying pressure to the solution when it is on one side of a selective membrane. More formally, RO is the process of forcing a solvent from a region of high solute concentration through a semipermeable membrane to a region of low solute concentration by applying a pressure in excess of the osmotic pressure. The result is that the solute is retained on the pressurized side of the membrane and the pure solvent is allowed to pass to the other side. The membrane is selective in that large molecules or ions are not allowed through the pores in the membrane, but allows smaller components of the solution (such as the solvent) to pass freely. RO filtration has various applications, including drinking water purification, wastewater purification, food industry uses (e.g., for concentrating food liquid), and health care uses (e.g., dialysis systems).

When RO systems are used for providing pure water to a dialysis machine or system issues of component contamination can arise when the pure water source system and the dialysis system have to be disconnected or separated, for instance, when the RO unit is used in a home patient situation where cleanliness is a concern and proper periodic disinfection is critical to patient health or in an RO unit servicing situation when both systems have to be reconnected. At the time of reconnection, the outlet hose or pipe from the pure water source system and the inlet hose or pipe from the dialysis machine may not be totally disinfected and now the operator must manually disinfect the transition point between the two systems with a chemical solution before it is returned to full service. Although the chemical solution and cleaning step may be effective, it is time consuming and the operator needs to flush out the system properly to ensure it is safe to be used on patients. The reconnection becomes an even greater challenge where portable RO machines are being used and such portable units are moved around within a facility or from one facility to the next and the operator needs to ensure that the portable device they intend to use is chemically cleaned (as well as microbial free/bug free) and thoroughly rinsed before patient use. Storage of portable RO units, when not chemically treated for storage, leads to tremendous buildup of active bugs and/or microbial elements.

Although all dialysis machines run their own heat disinfection cycle, there is still an area at the water inlet that is not included in this "self-heat disinfection" process. Therefore, it would be very advantageous to provide a chemical-free simple cleaning method of heat disinfecting all three critical areas: the RO unit, the pure water supply path, and the dialysis machine. It would also be highly advantageous to the market to provide a portable or standalone RO system with the capability to disinfect or sanitize any external device (e.g., dialysis machine) or an external port or portion physically disposed or located beyond the pure water source outlet. Further, it would also be advantageous to be able to conduct such a sanitizing or heat disinfecting process without the need for establishing a communications link between the reverse osmosis system and the external device or space being sanitized (forming a closed loop system), as well as without the need for using compatible or like brands (or models) of equipment, thereby allowing all users to be able to take advantage of such a feature.

SUMMARY

In one example embodiment, In one example embodiment, there is provided a method for sanitizing an external heat tolerant device with heated purified water coupled to an outlet of a heat sanitizable reverse osmosis (RO) system, the RO system having an inlet for receiving potable water from an external potable feed water supply and an internal storage tank for storing purified water, at least one RO membrane unit adapted to receive water from the potable feed water supply and configured to purify the water and deliver the purified water through a delivery conduit to the external heat tolerant device, the method including the step of activating a purified water flow control system configured to supply and regulate the purified water flow and thereafter initiating a variable frequency drive (VFD) pump coupled to the internal storage tank to operate at a first pumping rate until an average feed water supply temperature and a purified water flow rate is determined and then transitioning to a second pumping rate. The method also includes initiating VFD pump stabilization as a flow volume measuring sensor coupled to the purified water flow is triggered upon sensing a water flow below a predefined level and then controlling via controller module the flow of the purified water in the RO system before activating heating of the purified water to be delivered continuously and in a stable state to the external device. In addition, the method includes activating a heat power application system including a heating device for applying heat to the purified water flow initiated by the controller module which is communicatively coupled with the heat power application system, and delivering a heat sanitizing purified water flow with the pump continuously through to the external heat tolerant device. The method further includes regulating a back pressure of the heated purified water via a system control of internal fluid flow directing valves with the controller module such that the controller monitors and controls one or more of a speed of the pump, a water temperature, and a water pressure in a non-closed loop system with the external device during a heat forward process of disinfection of an inlet of the external device.

In various related example embodiments disclosed herein of the heat forward process, the flow remains unaffected by feed water disturbances and overall power disturbances once the RO system is restarted. While performing the heat forward process the controller module varies the amount of applied power with a controller to a direct contact inline heating element assembly with an integral thermal sensor disposed within a purified water heating chamber as a function of a sensed purified water temperature. Finally, in ending the heat forward process, a user activates an exit process of the RO system thereby turning off the heating element, emptying the storage tank and cooling water flow paths and returning RO system to an idle mode.

In another example embodiment, there is provided a RO and sanitizing system is provided for delivering heated purified water, the RO system having an inlet for receiving potable water from an external potable feed water supply and an internal storage tank for storing purified water, the RO system having at least one RO membrane unit adapted to receive water from the potable feed water supply and configured to purify the water and deliver the purified water through a delivery conduit. The RO system also includes a controller module designed to activate a heat sanitizing cycle within the sanitizing system, the controller module further including a heating power management control circuit configured to isolate the RO system and drive heated sanitized purified water solely through an external heat tolerant device of any brand or manufacturer. Sanitizing water is provided in a continual and stable manner regardless of external flow conditions. The RO system also includes a variable frequency drive (VFD) pump coupled to an RO membrane unit inlet and is communicatively coupled to the controller module, the VFD pump configured to operate at a first pumping rate until an average feed water supply temperature and pressure is determined and then transitioning to a second pumping rate. The VFD pump is further configured to draw water from the storage tank to stabilize the VFD pump from pressure fluctuations in the external feed water supply. The RO system further includes a solenoid valve and manifold assembly that is communicatively coupled to the controller module and to the VFD pump and is configured to control flow of the feed water supply and the purified water. The RO system, in this example embodiment, also includes a low flow velocity sensor communicatively coupled to the controller module and the VFD pump that is configured to initiate VFD pump stabilization. In a related embodiment, the RO system includes an inline heating element with an integral thermal sensor that raises the temperature of the water provided by the VFD pump to a first temperature and also includes a high flow pressure regulating control valve that is communicatively coupled to the controller module that regulates the water pressure from an outlet of the VFD pump flowing into the RO membrane unit. In one example embodiment, the heat forward system does not require a return port or conduit but the feed water temperature should be in a range of about 40° F. to about 100° F. (+/−1° F.) and the target temperature of the heated purified water is above 180° F., preferably 185° F. The minimum flow of feed water should also be about 800 ml to about 1000 ml/minute (but in some cases can be as low as 200 ml/minute). Once the flow target is reached the pump is locked in that pumping rate and the system uses the storage tank as the primary water source. In this example embodiment, the flow remains unaffected by feed water disturbances and overall power disturbances once the RO system is restarted. In a related embodiment, the method includes the step of varying amount of applied power with a controller to a direct contact inline heating element assembly with an integral thermal sensor disposed within a purified water heating chamber as a function of a sensed purified water temperature analyzed and processed by the controller module. In this embodiment, a user activates an exit process of the RO system thereby turning off the heating element, emptying the storage tank and cooling water flow paths and returning RO system to an idle mode.

In yet another example embodiment, there is provided a method for sanitizing an external heat tolerant device with heated purified water coupled to an outlet of a heat sanitizable RO system, the RO system having an inlet for receiving potable water from an external potable feed water supply and an internal storage tank for storing purified water, at least one RO membrane unit adapted to receive water from the potable feed water supply and configured to purify the water and deliver the purified water through a delivery conduit to the external heat tolerant device. The method includes the steps of activating a purified water flow control system configured to supply and regulate the purified water flow and of activating a heating power application system including a heating device configured to apply heat to the purified water flow and configured to deliver a heat sanitizing purified water flow continuously to the external heat tolerant device. The method also includes the step of initiating a variable frequency drive (VFD) pump coupled to the internal storage tank to operate at a first pumping rate until an average feed water supply temperature and a purified water flow rate is determined and then transitioning to a second pumping rate. The method further includes the step of initiating VFD pump stabilization as a flow volume measuring sensor coupled to the purified water flow is triggered upon sensing a water flow below a predefined level and providing a regulated flow of purified water by stabilizing the VFD pump from water pressure fluctuations in the external potable water supply by drawing water from the internal storage tank via an isolated storage tank. In a related embodiment, the method includes the step of controlling the flow of the purified water in the RO system before activating the heating of the purified water to be delivered continuously and in a stable state to the external device.

In yet another example embodiment, there is provided a method for sanitizing an external heat tolerant device with heated purified water coupled to an outlet of a heat sanitizable RO system, the RO system having an inlet for receiving potable water from an external potable feed water supply and an internal storage tank for storing purified water, and at least one RO membrane unit adapted to receive water from the potable feed water supply and configured to purify the water and deliver the purified water through a delivery conduit. The method includes the steps of activating a heating power application system including a heating device configured to apply heat to the purified water flow and configured to deliver a heat sanitizing purified water flow continuously through to the external heat tolerant device and initiating a variable frequency drive (VFD) pump coupled to the internal storage tank to operate at a first pumping rate until an average feed water supply temperature and a purified water flow rate is determined and then transitioning to a second pumping rate and providing a regulated flow of heated purified water by increasing or decreasing the VFD pumping rate as a function of water temperature fluctuations in the external potable water supply.

In any of the disclosed embodiments, the controller is communicatively coupled to a plurality of solenoid control valves and, with the VFD pump, regulates flow and water pressure applied to the RO membrane unit and thus production of heated purified water flow into and out of the external heat tolerant device or its inlet.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
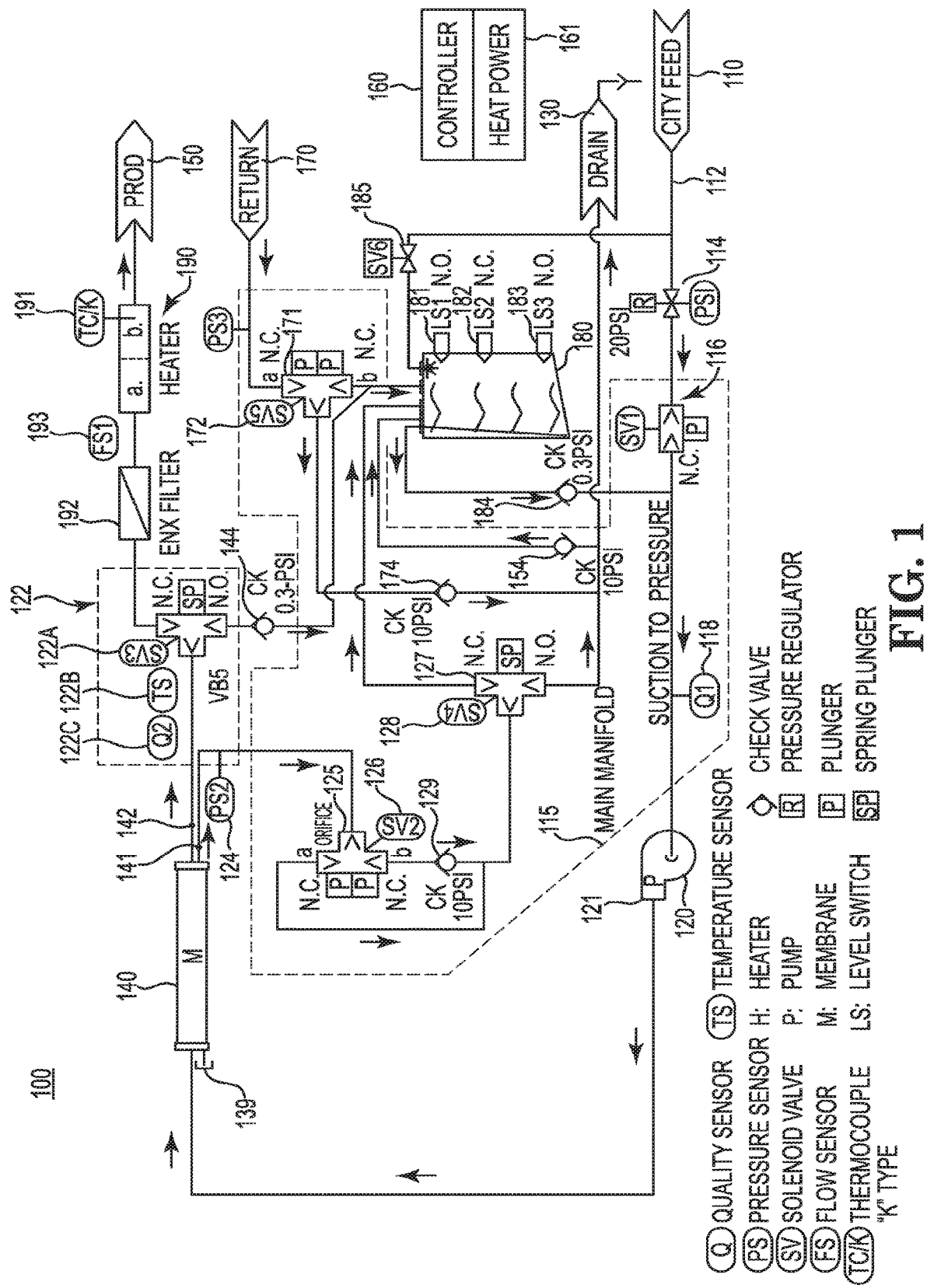
FIG. 1 is a schematic view of an embodiment of a RO water purification system having a heat forward capability for disinfecting an inlet of an external device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DESCRIPTION OF THE PREFERRED EMBODIMENTS

Figure 2:
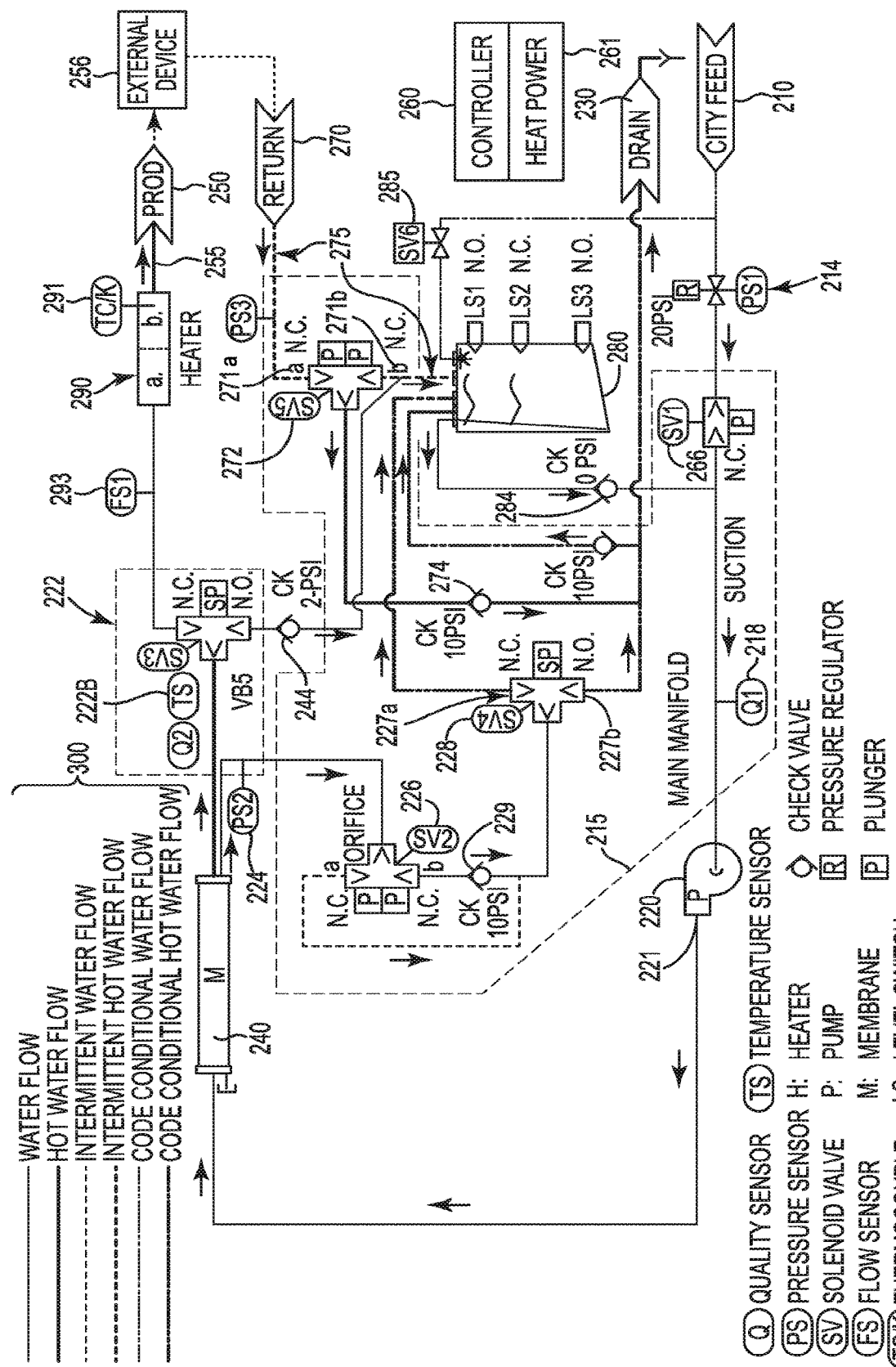
FIG. 2 is a schematic view of an example embodiment of a RO water purification system having a heat forward capability for disinfecting an external device as shown.

Referring now to the Figures, FIGS. 1 and 2 illustrate schematic views of an embodiment of a RO water purification system having a heat forward capability for disinfecting an external device and the associated fluid flows through the system, respectively. The RO system 100 purifies water provided by a feed water supply 110 for use in various applications, such as dialysis. The RO system 100 possesses monitoring for feed water pressure, feed water quality, feed water temperature, pump outlet pressure, product water pressure, product water temperature, product water quality, and membrane performance (percent rejection), while RO system 200 more specifically discloses the heat forward function and the associated flows with the controlling components in the system. A variable frequency pump 120 provides the pressure required to push water through the RO membrane and against a fixed orifice, while fluid controls along with a controller 160 provide a means of managing flow rates and pressures. In particular, RO system 100 provides for sanitizing with heated purified water, with the RO system having an inlet 112 for receiving potable water from an external (city) potable feed water supply 110 and an internal storage tank 180 for storing purified or potable water (and/or a combination of both depending on the active process), the RO system having at least one RO membrane unit 140 that receives water from potable feed water supply 110 and which purifies the water and delivers the purified water through delivery conduit 142 (and delivers concentrate or waste water through conduit 141 and main manifold 115) and eventually provides purified product water at product water outlet 150. RO system 100 also includes a return outlet 170 for directing excess or unused product water through manifold 115 to storage tank 180 or to a drain outlet 130. Drain outlet 130 can also receive waste water from membrane 140. The drain output 130 may be connected to a receptacle or other system for proper disposal of the drain fluid.

In this example embodiment, RO system 100 also includes controller module 160 which activates a heat sanitizing cycle within the sanitizing system and that is programmed to operate the components of the system 100 to provide various functionalities (e.g., water purification, sanitization, etc.). Controller module 160 further includes a heating power management control circuit 161 programmed to help isolate part of RO system 100 and drive heated sanitized purified water solely through an external heat tolerant device (heat forward function), such as a dialysis machine or other heat tolerant device or heat tolerant section or portion (device 256 in system 200) of an overall system (not shown in system 100). A challenge with most prior art RO systems and dialysis machines is found in an external connection section of most dialysis machines when trying to connect the dialysis machine to an RO system—this external connection or portion being called "no man's land"—as an operator has to remember to separately sanitize or disinfect this area or connection section between the RO system and the dialysis machine. With the various RO systems described herein, this external connection section can be cleaned and disinfected with the heat forward process by using heated purified water that is directed to the non-sterilized connection section, with the right temperature, time and flow, to thoroughly clean and disinfect this external connection section. Such cleaning/disinfection can now be advantageously performed without the need for, as in current RO systems and cleaning accessory combinations, direct/indirect or wired/wireless closed-loop communication between RO system 100 and the dialysis unit (or external heat tolerant device) or the need to introduce a chemical cleaner or process that would need further rinsing after chemical disinfection.

Prior art systems require the closed-loop system, between the dialysis machine and the RO sanitizing system in order to overcome stability issues of controlling the water temperature as heating water can quickly turn into a dangerous situation of the temperature escalates to quickly or running indefinitely or exceeding the system's heat rating or capability (potential for building up too much steam). The heat forward system described herein very closely controls and monitors the heating of the product water through controller 160 and 260 and the various sensors; and flows through the system are monitored closely to look for disturbances and to monitor any pressure potentially building up in the system. An altering or reduction in the heating power application and/or altering a return flow path using one of the solenoid valves and check valves helps to bring RO system and the heat forward process back under control. Any levels that reach maximum current draw for any of the heating elements are managed immediately by controller 160/260 so as to limit the current. Further, a control of the pump speed of pump 120/220 or control of the flow path also within the purview of the capabilities of controller 160/260.

Referring again to FIGS. 1 and 2, in this example embodiment of RO system 100, a series of solenoid valves (SV), check valves (CK) and conductivity sensors (Q) are housed in main manifold 115 to facilitate precise control of heating and cooling flows throughout the RO system and also facilitate the heat forward process, hence a detailed description of these components is provided in connection with FIG. 1. Solenoid valve (SV1) 116 is a rinse water solenoid that is a normally closed valve used during the purge, rinse and the heat forward process. It is also open if there is not enough water in the internal water tank during normal dialysis operation. Solenoid valve (SV2) 126 is a waste water valve assembly that includes two solenoids. During normal dialysis operation SV2a is closed and water flows through the orifice hole. The valve is open during flushing, chemical and heat disinfection processes. On the other hand, solenoid valve SV2b opens during the heat forward process to provide a specific amount of backpressure on the membrane. Solenoid valve (SV3) 122A is a product water solenoid that is normally closed. During startup, the water flow is diverted. Once the product water quality improves below the product water quality alarm, it opens and supplies water to the product line. Solenoid valve (SV4) 128 is a waste recycle control solenoid which is a 3-way valve that directs waste flow to the drain of the RO system. This valve can recycle waste water into the internal tank when the RO system is set up for the water saver function. Solenoid valve (SV5) 172 is a product water return solenoid valve having two solenoids: a) solenoid SV5a provides backpressure during normal operation of the RO system allowing it to supply product water at a pressure of approximately 30 PSI. During heat and chemical modes, this valve is open allowing full flow for proper operation; and b) solenoid SV5b allows product water to the tank or direct to drain. Finally, solenoid valve (SV6) 185 is an inlet water solenoid valve which provides feed water to the internal tank during operation of the RO system during chemical rinse, heat forward and normal dialysis processes. During a heat forward disinfecting process, solenoid valve 126 opens to help configure RO system 100 at a predetermined condition of flow during the heat forward process.

Referring again to FIGS. 1 and 2, a series of check valves are provided that operate with the various solenoid valves and controller 160 to control the various flows for the heat forward process. A check valve CK1, which is located on the waste side of the membrane, provides backpressure during the heat forward process. A check valve CK2, which is located between the drain line and solenoid valve (SV5) 172, prevents waste water from entering the product line 150. A check valve CK3, which is located between the internal tank 180 and drain 130, will divert water to the tank if the drain line is obstructed. A check valve CK5, which is located in the tank outlet path to the pump 120, prevents RO feed water 110 from being fed into internal tank 180.

RO system 100 also includes a series of conductivity sensors (Q) which are in communication with controller 160 as well as the solenoid valves and check valves to control flows within system 100. An RO feed water conductivity sensor (Q1) 118 which monitors the quality and temperature of the inlet water to pump 120. Inlet water quality and temperature can be viewed from an ANALOG screen on the RO system display/GUI (user interface). The value is compared to the product water quality reading to calculate the percent rejection and is a temperature compensated sensor. A product water conductivity sensor (Q2) 122C monitors the quality and temperature of the water after it exits the membrane 140. Product water quality can be viewed from a RUN screen during normal operation and the value is compared to the inlet water quality reading to calculate the percent rejection. Temperature can also be viewed from the ANALOG screen of the RO system 100 display and this sensor is also temperature compensated. An RO feed water pressure sensor (PS1) (near regulator 114) monitors the incoming water pressure to the RO system 100 and will shut down the RO system if there is low or high RO feed water pressure. The feed water pressure can be viewed from the ANALOG screen. A pump outlet pressure sensor (PS2) 124 monitors the output of the pump 120 and will shut down the RO system if an over-pressure or under-pressure condition is sensed. The pump outlet pressure can be viewed from the RUN screen of the system display and pump pressure can also be viewed from the ANALOG screen. A product water pressure sensor (PS3-near return 170) monitors the product water pressure and will shut down the RO system if an overpressure condition is detected. The product water pressure can be viewed from the RUN screen or from the ANALOG screen. A pressure regulator (PR) 114 controls the incoming feed pressure to the RO system when solenoid valve (SV1) 116 is open. A flow sensor (FS1) 193 switch monitors the flow of product water from the membrane 140, thereby displaying flow on the RUN screen or the ANALOG screen. A thermocouple (TC/F) 191, which is located near the heater 190, monitors the temperature of the water exiting the heater. The temperature is displayed on the RUN screen and can also be viewed from the ANALOG screen.

In this example embodiment, RO system 100 also includes a variable frequency drive (VFD) pump 120 that is coupled to an RO membrane unit inlet 139 and that is communicatively coupled to controller module 160. Pump 120 generally controls the fluid pressure through RO system 100 and generally controls water pressure input to membrane 140. In some embodiments, pump 120 maybe a pump other than a VFD pump and has a pump pressure of about 160-200 pounds per square inch (psi) (1.10-1.24 MPa). In some embodiments, a pump includes a pressure sensor used to control the operation of VFD pump 120 so as to shut down system 100 if an overpressure condition is detected. In this example embodiment, VFD pump 120 is designed to operate at a first pumping rate until an average feed water supply temperature and pressure (provided by city feed 110) is determined and once an appropriate predefined temperature and pressure is achieved then transitioning to a second pumping rate. VFD pump is further designed to draw water from storage tank 180 to stabilize VFD pump 120 from pressure fluctuations in external feed water supply 110. RO system 100 further includes a solenoid valve and manifold assembly 115 that is communicatively coupled to controller module 160 and to VFD pump 120, the main manifold being configured to control flow of feed water supply 110 via line 112 and the purified water provided by membrane unit 140 via delivery conduit or outlet 142.

Referring again to FIG. 1, during a normal water purification cycle, the solenoid valve 185 (and alternatively valve 116) cycles depending on the level of water in the tank 180. During heating and chemical sanitization modes of operation, described in more detail below, the solenoid valve 116 operates independently to isolate the pump 120. The quality sensor 122C and temperature sensor 122B monitor the quality and temperature of the product water, respectively, after the pure product water exits membrane 140. The product water quality measured by the quality sensor 122C can be reviewed (e.g., on a screen associated with the system 100) during normal operation. The input of a check valve 144 is connected between the output of the membrane 140 via the valve body 122A, and an output of check valve 144 is connected to the input of internal tank 180. Check valve 144 is configured to prevent backflow of water in internal tank 180 into the product water provided to the product water output 150 and simply blocks back flow into the divert valve 122a. In another part of the system, a solenoid valve 172a provides fluid flow resistance during normal operation to the unused product water returning from the external connection 170. Check valve 174 is configured to prevent backflow of water in internal tank 180 into return water input 170. In some embodiments, the solenoid valve 172 provides a backpressure to maintain the product water at a pressure of approximately 35 psi (0.241 MPa). Check valve 184 is configured to prevent backflow of water in internal tank 180 from city feed water supply 110. Check valve 154 is configured to provide a flow path into tank 180 for waste flow if the drain 130 becomes blocked or restricted. Check valve 184 is at an outlet of tank 180 and prevents pressurized potable water from entering tank 180 when valve 116 is open and feeding pump 120 directly. Check valve 174 is connected between drain output 130 and valve 172 and is configured to prevent back flow from drain 130 into valve 172 and or provide a restricted forward flow from valve 172 to drain 130; dependent on process conditions. A solenoid valve 185 is controllable to provide potable water flow into tank 180; depending on process conditions.

In some embodiments, RO membrane 140 is a single membrane comprised of a polymeric material and may include a dense layer in a polymer matrix, such as the skin of an asymmetric membrane or an interfacial polymerized layer within a thin-film-composite membrane, where the separation of the product water from the waste water occurs. Membrane 140 may have a variety of configurations including, for example, spiral wound or hollow fiber configurations. Outputs 141 passes through product water manifold 122 into the larger main manifold 115 and valve 126 at 125 and with the valve 126a closed flows through an internal orifice to valve 128. The flow through 142 enters product water manifold 122 and valve 122a and flows to 192 or 144 depending on process and water quality conditions. A check valve 129 prevents backflow from the storage tank and recirculating into valve 126b.

In operation, a purified water flow control system as part of RO system 100 supplies and regulates the purified water flow as well as activates a heating power application system from the heat power module 161. Heater element 190 applies heat to the purified water flow and through a heat forward process delivers a heat disinfecting purified water flow continuously through to the external heat tolerant device. In operation, variable frequency drive (VFD) pump 120 that is operatively coupled to the internal storage tank is initiated and operates at a first pumping rate until an average feed water supply temperature and a purified water flow rate is determined and then pump 120 transitions to a second pumping rate. VFD pump 120 stabilization is initiated as a flow volume measuring sensor 193 coupled to the purified water flow is triggered upon sensing a water flow below a predefined level and provides a regulated flow of purified water by stabilizing VFD pump 120 from water pressure fluctuations in the external potable water supply 110 by drawing water from the internal storage tank 180 via an isolated storage tank feed. In a related embodiment, this condition occurs when the external potable water pressure falls below a predefined water pressure level.

Controller 160 initiates raising the temperature of the regulated purified water flow provided by VFD pump 120 via the internal inline heater element to a predefined level above a fixed minimum temperature of about 80° C. for disinfecting the external heat tolerant device. In a related embodiment, controller 160 varies the amount of applied power to a direct contact inline heating element assembly with an integral thermal sensor disposed within a purified water heating chamber as a function of a sensed purified water temperature. Controller 160 further regulates the purified and heated water flow and pressure into and out of the external heat tolerant device and monitors the water temperature so as to increase or decrease a VFD pump rate to maintain the water temperature at a defined level. Controller 160 also regulates a back pressure of the supplied heated purified water via a system control of internal flow directing check valves and assists in the collection of a redirected flow of heated purified water and unused heated purified water into internal storage tank 180.

Controller 160 provides various operating modes to compensate for a reduction in heated purified water flow in the RO system. Upon sensing a reduction in heated purified water flow below a predetermined level, controller 160 initiates controlling heated purified water flow and temperature within a heating chamber by opening multiple valves on a return side of the heated water flow and increasing the VFD pump rate so as to increase heated water flow velocity. In the instance where the heated purified water temperature fluctuates above or below a defined temperature range, controller 160 initiates adjusting heating power values up or down for a predetermined time and then further monitors a number of water temperature fluctuations above and below the defined temperature range during a defined time period when the number of fluctuations exceeds a defined number during a defined time. Controller 160 also allows the user to manually activate an exit process of the RO system 100 thereby turning off the heating element, emptying the storage tank and cooling water flow paths and returning RO system to an idle mode.

In a related embodiment, controller 160 initiates activating a heating power application system of heat power controller 161 including a heating device configured to apply heat to the purified water flow and configured to deliver a heat sanitizing purified water flow continuously through to the external heat tolerant device and initiating a variable frequency drive (VFD) pump coupled to the internal storage tank to operate at a first pumping rate until an average feed water supply temperature and a purified water flow rate is determined and then transitioning to a second pumping rate and providing a regulated flow of heated purified water by increasing or decreasing the VFD pumping rate as a function of water temperature fluctuations in the external potable water supply. Controller 160 controls the flow of the purified water in RO system 100 before activating the heating of the purified water to be delivered continuously and in a stable state to the external device. Upon the heated purified water temperature fluctuating above or below a defined temperature range, heating power values are adjusted up or down for a predetermined time and then further monitoring is initiated of the number of water temperature fluctuations above and below the defined temperature range during a defined time period when the number of fluctuations exceeds a defined number during a defined time. In one example embodiment, controller 160 assists in operating RO system 100 with low inlet pressure from the external feed water supply without shutting down system 100 (as well as system 200 below).

Referring now to FIG. 2, more specifically there is illustrated a schematic view of an example embodiment of a RO water purification system 200, illustrating the fluid flows for the heat forward process of system 100, (having a heat forward capability for disinfecting an external device 256. In particular, process 200 drives product hot water flow at the product flow outlet 250 via conduit 255 and directs return 270, via conduit 275, hot water via main manifold 215 to the storage tank 280 or to the drain output 230. The drain output 230 may be connected to a receptacle or other system for proper disposal of the drain fluid. In particular, RO system 200 provides for sanitizing with heated purified water the external connection ("no man's land") to the external device 256 with water primarily sourced from storage tank 180. RO system also includes a return outlet 270 and conduit 275 for directing excess or unused product water to storage tank 280 or to a drain outlet 230. Drain outlet 230 can also receive waste water from membrane 240.

Referring again to FIG. 2, in this example embodiment, controller module 260 of RO system 200 not only activates a heat sanitizing cycle within the sanitizing system as well as managing the heat power management control circuit 261 but controller 260 also helps to isolate part of RO system 200 and drive heated sanitized purified water solely through an external heat tolerant device 256, such as a dialysis machine or other heat tolerant device or heat tolerant section or portion of an overall system, which is coupled to system 200. Upon the user of RO system 200 selecting the heat forward process via the system GUI (user interface), pump 220 ramps up mainly flowing concentrate through solenoid valve 226, through check valve 229 and inlet valve 227 and out through drain 230. Pump 220 further starts moving some volume of pure product water through flow sensor 293 to and out of product outlet 250 and through external device 256 (or the external connection). After flowing through inlet of external device 256, the product water returns to return 270 and flows through solenoid valve 272 via inlet valve 271a and through outlet valve 217b, and then flows through check valve 274 and out to drain 230 or flows to tank 280. Once flow is sensed by flow sensor 293, pump 220 continues to 'tune' for a flow rate pre-determined by flow sensor 293 and controller 260 as a function of the temperature measured at quality sensor 218. Once the target fluid flow rate is stabilized, pump 220 locks its pumping action conditions. Thereafter, with pump 220 in a locked mode, controller 260 initiates the heating of product water flow 250 by a signal to heating power module 261 which in turn signals inline heater 290 and thermocouple 291 to initiate heating and heat monitoring.

During all of the heat forward processes (including start-up, running and heat forward cool down), city feed water 210 is always provided via line 212, and through solenoid valve 285, and fluid levels usable in the RO system are sensed by water level sensors 281, 282, 283 of storage tank 280. Internal tank 280 receives water from check valve 244 and/or the return input 270. The level of the fluid in internal tank 280 is measured by the level sensors 281, 282 and 283 with level sensor 281 being triggered when water in tank 280 is at or above a maximum water level, level sensor 282 being triggered when water in tank 280 is at or below an intermediate water level, and level sensor 283 being triggered when the water in tank 280 is at or below a minimum water level. Outflow from storage tank 280 then occurs through check valve 284 and the inlet of pump 220. Concentrate flow is discharged to drain 230 via a flow to and through solenoid valve 226 and then through check valve 229 and through valve 227 of solenoid valve 228. Precise water product flow 250 and thermal stability, under all circumstances, is provided via input signals from sensor 218, temperature sensor 222B, pressure sensor 224, flow sensor 293, pressure sensor PS3 at outlet of return 270 and an algorithm uploaded to controller 260, which precisely controls the operations of solenoid valve 228 (and individual valves 271a and 271b), inline heater 290 and thermocouple 291, and pump 220.

In the above embodiments, controller 260 is communicatively coupled to a plurality of solenoid control valves and with VFD pump 220 and as a system regulate flow and water pressure applied to RO membrane unit 240 and thus production of heated purified water flow into and out of the inlet of external heat tolerant device 256 (such as a dialysis machine). The controller is also communicatively coupled to a plurality of solenoid control valves and with the VFD pump so as to regulate flow and water pressure applied to the RO membrane unit and distribution of heated purified water flow throughout the RO system and control and senses fluid outflows out of system 200.

After the external connection or external heat tolerant device is sanitized, a user can initiate a stop of the heat forward process or select "EXIT" procedure, at which time system 200 will automatically proceed to cool itself down via a heat forward cooling cycle in which water flows primarily from, but is not necessarily limited to, city feed 210. In a related embodiment, water from the storage tank 280 can also be used to cool the system. Water from city feed 210 flows through main manifold 215 and is pumped with pump 220 through membrane 240 through to product outlet 250 (and through heater 290) and returns through return port 270 and back through to storage tank 280. Waste water from membrane 240 also flows back through main manifold 215 and through solenoid valve 226 and check valve 229 and through solenoid valve 228 and out to drain outlet 230.

In a related embodiment, the heat forward system 200 uses storage tank 280 in either break tank mode or it can go directly into a multimode configuration. The heat forward process typically operates at temperatures above 185° F. and can commence as soon as the water temperature is above 185° F. Once the water temperature reaches its target temperature, it locks onto the target and begins flow stability within system 200. A target temperature of system 200 is dependent on the feed water temperature provided to as system 200 determines as a function of the feed water temperature how much pure water that it can produce, at what volume and at what flow rate. The colder the feed water temperature, the slower and lower the amount of pure water that system 200 will be able to produce in a certain time-frame as cold water takes longer to permeate membrane 140 or 240 than does warmer water. A key advantage is that system 200 can be stable in the heating process due to the low amount of water in the system and due to the stabilization of the flow and stabilization of the pump. In one example embodiment, where the feed water temperature is cold and flow is stable (with the help of solenoid valve (SV5) 272), system 200 can estimate generating about 200 ml/minute of flow of product water. Hence, manipulating SV5 and slowing down the operation of pump 120 helps to control any potential pressure build-up in system 200. If there is a disturbance in the water temperature, controller 260 along with the various temperature sensors and solenoid valves will drive promptly towards system control and stability by monitoring the current fluid flow within system 200. Further, system 200 shuts down if there is a loss of power as system 200 is configured for manned operation. In one example embodiment, system 200 can reach a target temperature of about 185° F. for heat forward sanitization or for the self-heating process in about 30 minutes depending on the size hose or conduit used in the external connection portion and the temperature of the feed water being used. System 200 will take will take longer to reach a desired pure water generation level depending on the water feed temperature and on the hose length depending on whether the hose used is longer between the dialysis machine and the RO system generating the heat forward water.

In this example embodiment, RO system 200 includes a low flow velocity sensor assembly 203 which senses if flow in the line is substantially slowing down, and also protects an inline heater 290, is communicatively coupled to controller module 260 and VFD pump 220 that is configured to initiate VFD pump stabilization should there be fluctuations in water pressure from city feed 210. In this example embodiment, RO system 200 also includes an integral thermal sensor 291 that quickly raises the temperature of RO water provided by VFD pump 220 and membrane 240 to a first temperature as a function of a sensed purified water temperature. Unlike previous RO systems that have had the heater element located in the storage tank, moving the heater element out of the storage tank facilitates precise control of the temperature of the purified product water being delivered by RO system 200 and reduces power requirements as only the water that is needed is heated and not the entire storage tank 280 as in other RO systems. In this example embodiment of RO system 200 there is also included a high flow pressure regulator 214 that is communicatively coupled to controller module 260 and which regulates water pressure from city feed 210 and flow sensor 293 that monitors an outlet 221 of VFD pump 220 flowing into RO membrane unit 240.

Further in the above example embodiment, upon sensing an overheating condition in system 200, controller 260 monitors the water temperature so as to increase or decrease a VFD pump rate to maintain the water temperature at a defined level and upon sensing a reduction in heated purified water flow below a predetermined level, controller 260 proceeds to control the heated purified water flow and temperature by opening multiple valves (primarily solenoid valves) on a return side of the heated water flow and increases the VFD pump rate so as to increase heated water flow velocity thereby eliminating the overheat condition. So as not to have a runaway heating or pressure condition within system 200, upon the heated purified water temperature fluctuating above or below a defined temperature range and being sensed and acknowledged by controller 260, controller 260 proceeds to adjust the heating power values up or down for a predetermined time and then further monitors a number of water temperature fluctuations above and below the defined temperature range during a defined time period when the number of fluctuations exceeds a defined number during a defined time. This constant monitoring by controller 260 and associated sensors assists in keeping system 200 stable and in control.

One of the main advantages of system 200 and the heat forward method and system taught herein is that fluid outflow from product port 150/250 and any other port or orifice of system 200 is controlled and monitored by controller 160, allowing system 200 to work independently of the dialysis machine (or any other external device) that system 200 is connected to. When solenoid valve (S5) 272 leading to tank 280 but also connected with return 270 at the other end, is open and the fluid flow from external device 256 stops, then controller 260 senses that external device 256 is longer taking water (or the internal solenoid valve is closed and/or their internal tank is full), solenoid valve 272 then adjusts the return path and begins to direct water back through to return port 270 and back to tank 280. This capability also allows system 200 to control the outflow of heated water by using SV5a to direct water to tank 280 or using SV5 to direct water to drain 230. In this example, such outflow control if facilitated by the use of a Y-connector to the hose going from product port 250 to external device 256 (one branch) and to return port 270 (second branch).

Figure 3:
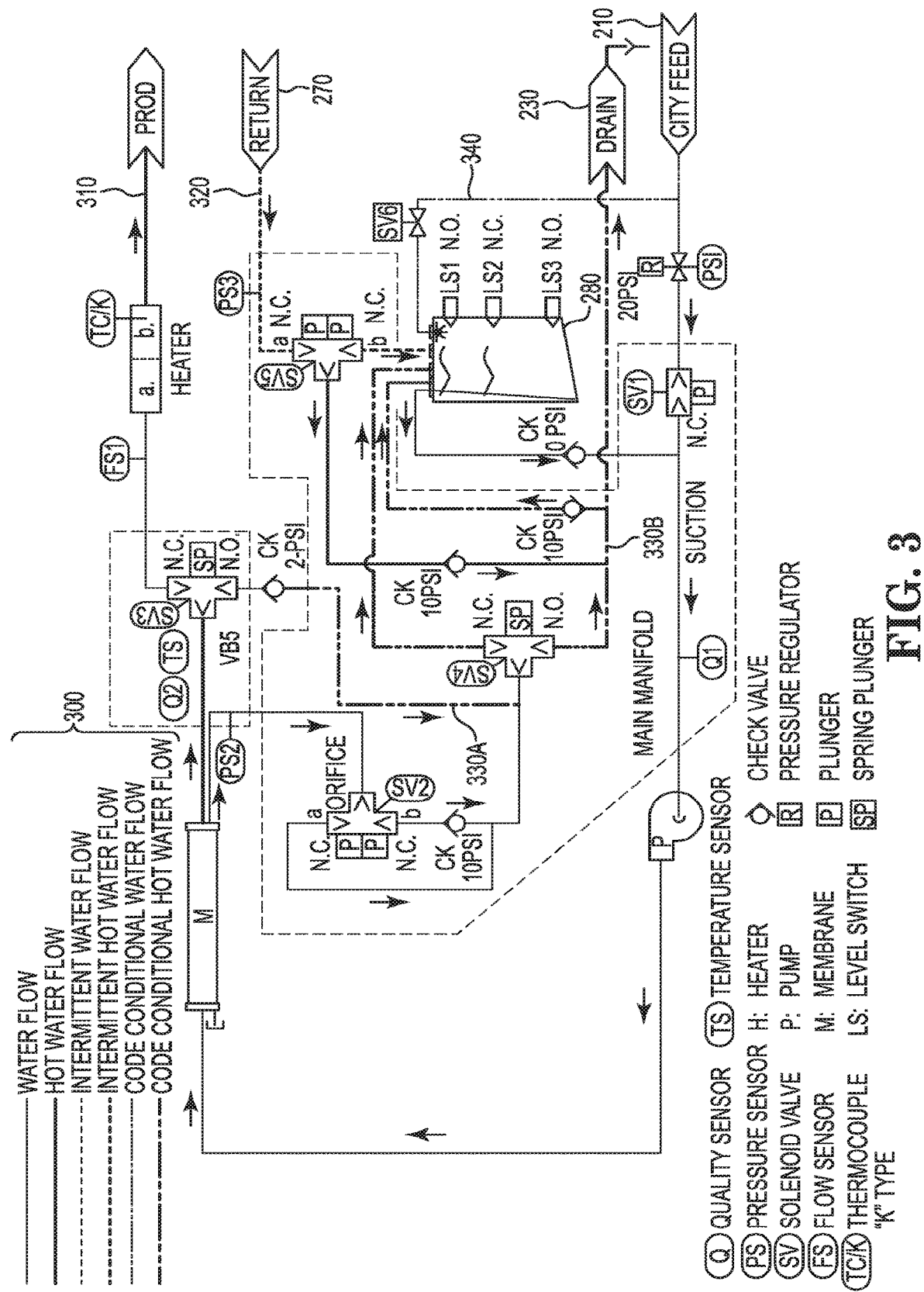
FIG. 3 is a schematic view of the RO system operating to provide a dialysis machine pure water.

FIG. 3 is a schematic view of RO system 200 operating to provide an external device (e.g., dialysis machine) with pure water. Note from a line code 300 provided on the upper left hand corner describing the various operating conditions of the RO systems described herein. In this example embodiment, product water flows 310 out and there is an intermittent water flow 320 from the return port 270. There is also a conditional water flow 330A that flows to storage tank 280 and a water flow 330B that flows out to drain port 230. An alternate flow is also provided through solenoid valve SV5 from return 270 out to either tank 280 or out to drain 230. Waste water can also flow from membrane 240 through SV2 and through its orifice when the solenoid coils are not energized though to solenoid valve (SV4) 128 and then out to either drain 230 or upper path back to tank 280. Finally, there is a water flow 340 from city feed 210 back to storage tank 280.

Figure 4A:
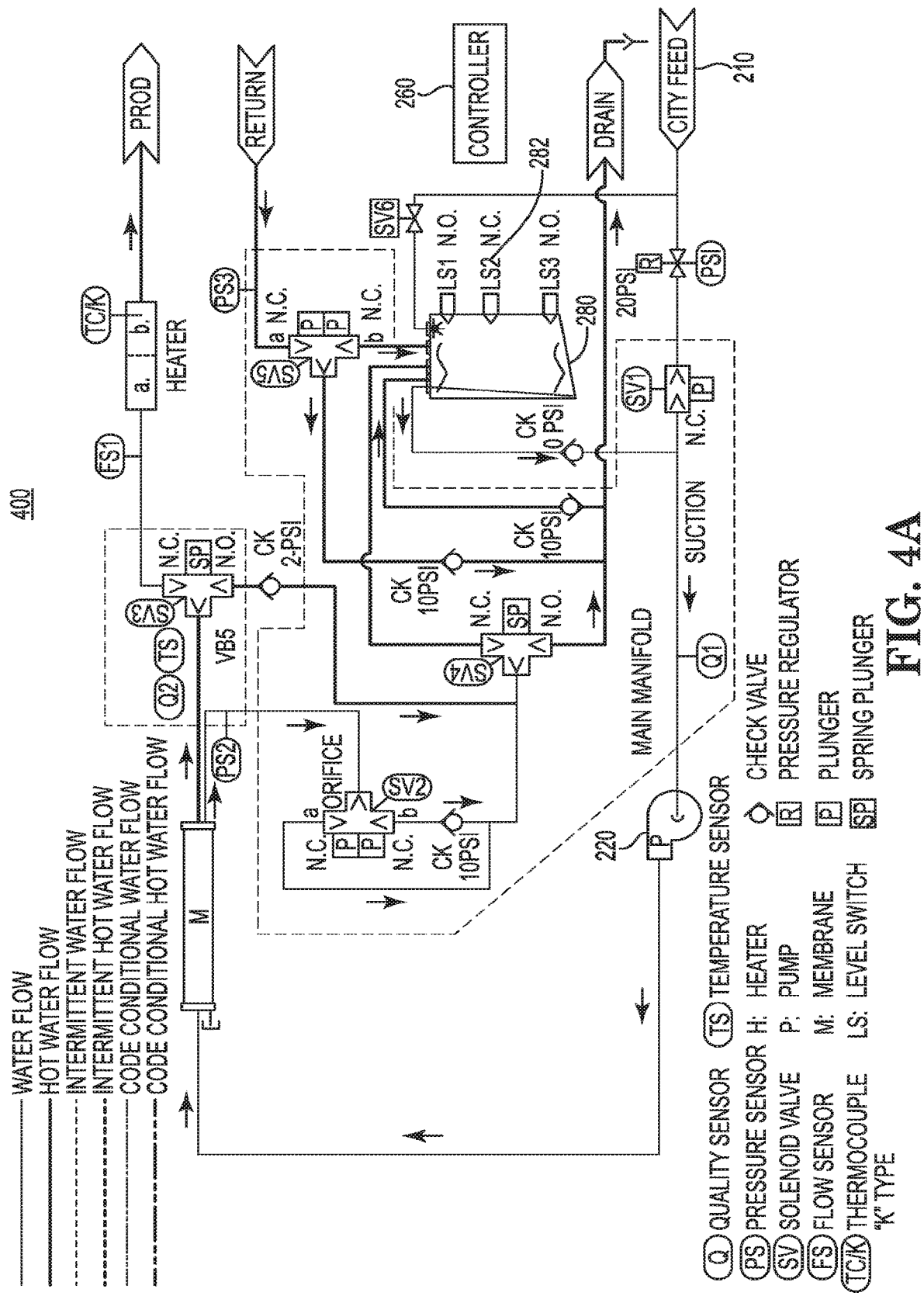
FIG. 4A and 4B are schematic views of the RO system running a purge operation of a pure water storage tank and refilling the pure water storage tank with pure water, respectively.
Figure 4B:
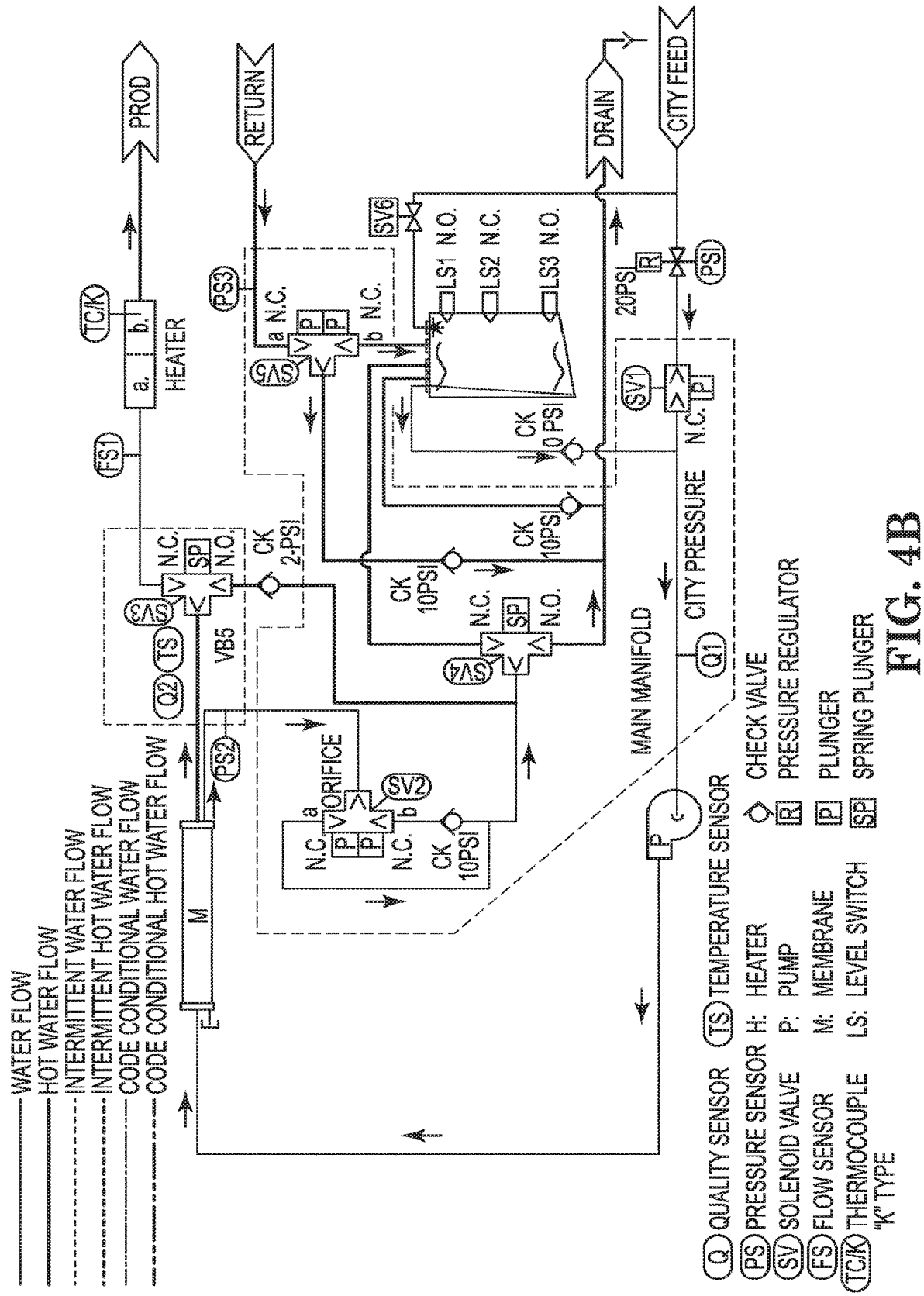

FIGS. 4A and 4B are schematic views of the RO system running a purge operation 400 of a pure water storage tank and refilling the pure water storage tank with pure water, respectively. In this example embodiment, storage tank 280 is first emptied then pump 220 is engage via controller 260 to energize solenoid valve SV1 to allow city water 210 to flow through to pump 220. FIG. 4A the check valve is open for storage tank purge but is closed in FIG. 4B when refilling storage tank. Tank 280 is then refilled and water is pushed around the various conduits of system 200 to continue with purge operation. Once level switch (LSI2) 282 is activated at about half of the tank refill level, controller 260 is signaled to stop pushing water through system 200. Once purge is complete, chemical cleaning/purge or self-heat cleaning can continue.

Figure 5:
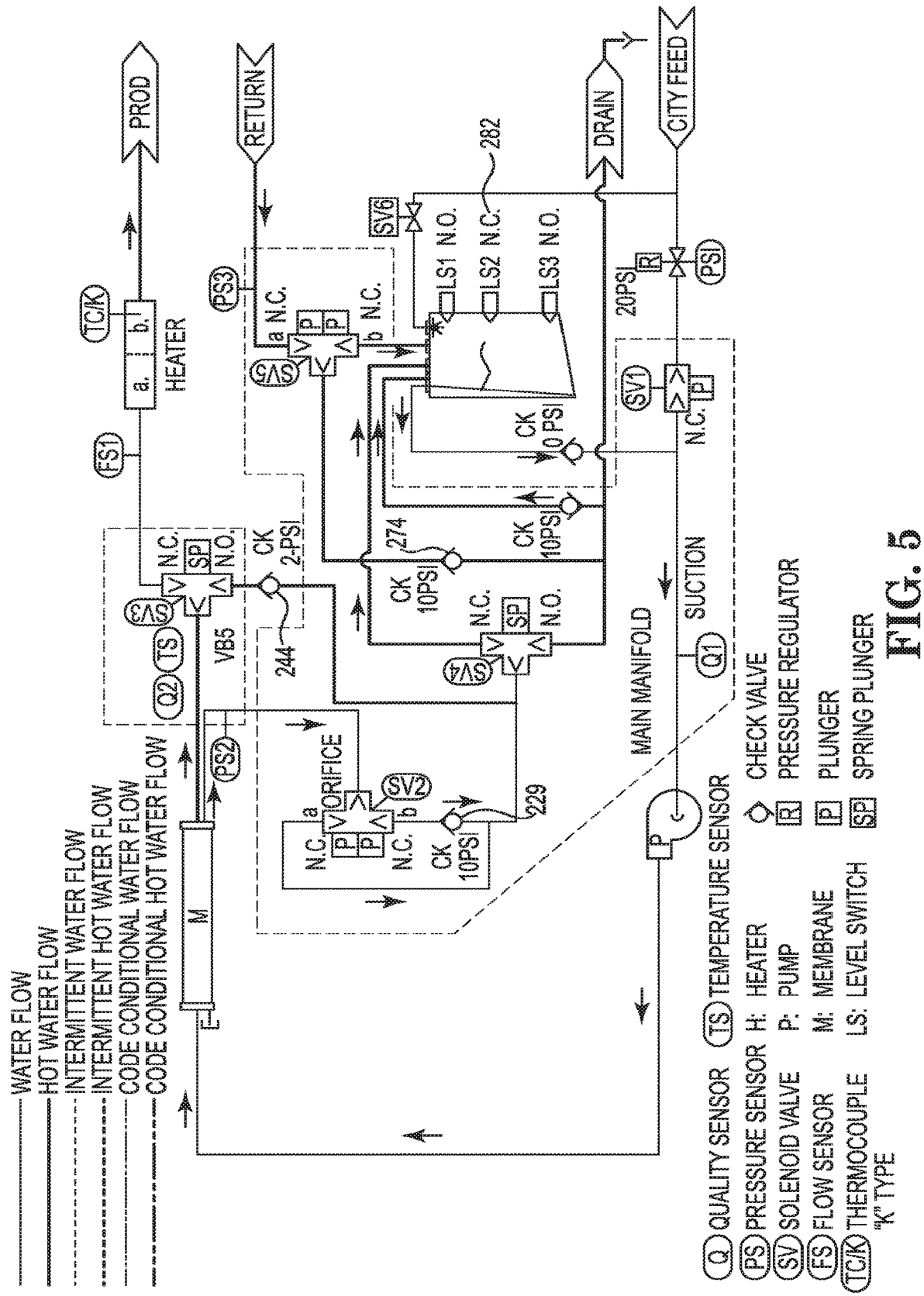
FIG. 5 is a schematic view of the RO system recirculating heat sanitizing water through components of the RO system.

FIG. 5 is a schematic view of RO system 200 recirculating heat sanitizing water through components of the RO system. In this example embodiment, check valve 229 closes off line 241 from membrane 240, check valve 244 closes off any back from the outgoing product water line and check valve 274 closes off any backflow from the return line. Storage tank level sensor 282 stays on to measure the storage tank level to ensure there is sufficient water to run the heat circulation process.

U.S. Patent Publication No. 2014/0151297 filed on Nov. 27, 2013 is incorporated herein by reference in its entirety.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

I claim:

1. A reverse osmosis (RO) system configured for sanitizing an external heat tolerance device with heated purified water, the RO system having an inlet for receiving potable water from an external potable feed water supply and an internal storage tank for storing purified water, the RO system having at least one RO membrane unit adapted to receive water from the potable feed water supply and configured to purify the water and deliver the purified water through a delivery conduit, the RO system comprising:

a controller module configured to activate a heat sanitizing cycle within a sanitizing system, the controller module further including a heating power management control circuit configured to isolate the RO system and drive heated sanitized purified water through to the inlet of an external heat tolerant device;

a variable frequency drive (VFD) pump coupled to an inlet of the at least one RO membrane unit and communicatively coupled to a controller module, the VFD pump configured to operate at a first pumping rate until an average feed water supply temperature and pressure is determined and then transitioning to a second pumping rate, the VFD pump further configured to draw water from the storage tank to stabilize the VFD pump from pressure fluctuations in the external feed water supply;

a solenoid valve and manifold assembly communicatively coupled to the controller module and to the VFD pump, the controller module configured to control flow of the feed water supply and the purified water; and a low flow velocity sensor communicatively coupled to the controller module and the VFD pump and configured to initiate VFD pump stabilization upon sensing a purified water flow below a predefined level.

2. The RO system of claim 1 further comprising an inline heating element with an integral thermal sensor configured to raise the temperature of the reverse osmosis purified water.

3. The RO system of claim 1 wherein the controller module is communicatively coupled to a plurality of solenoid control valves and with the VFD pump and is adapted to regulate flow and water pressure applied to the at least one RO membrane unit and thus production of heated purified water flow into and out of the inlet of the external heat tolerant device.

4. The RO system of claim 1 wherein the controller module is communicatively coupled to a plurality of solenoid control valves and with the VFD pump and is adapted to regulate flow and water pressure applied to the at least one RO membrane unit and distribution of heated purified water flow throughout the RO system.

5. The RO system of claim 1 wherein the external heat tolerant device includes a dialysis machine.

* * * * *